United States Patent [19]
Reefman

[11] Patent Number: 6,108,401
[45] Date of Patent: Aug. 22, 2000

[54] METHOD OF STANDARD-LESS PHASE ANALYSIS BY MEANS OF A DIFFRACTOGRAM

[75] Inventor: Derk Reefman, Eindhoven, Netherlands

[73] Assignee: U.S. Philips Corporation, New York, N.Y.

[21] Appl. No.: 09/216,255

[22] Filed: Dec. 18, 1998

[30] Foreign Application Priority Data

Dec. 22, 1997 [EP] European Pat. Off. .............. 97204064

[51] Int. Cl.⁷ .................................................. G01N 23/00
[52] U.S. Cl. .............................................. 378/83; 378/71
[58] Field of Search ................................. 378/70, 71, 73, 378/75, 82, 83, 86, 88

[56] References Cited

U.S. PATENT DOCUMENTS

| | | | |
|---|---|---|---|
| 3,961,186 | 6/1976 | Leunbach | 250/272 |
| 4,592,082 | 5/1986 | Pawloski | 378/75 |
| 4,991,191 | 2/1991 | Suryanarayanan | 378/75 |
| 5,812,630 | 9/1998 | Blaffert | 378/83 |

OTHER PUBLICATIONS

"A Method of Quantitative Phase Analysis Without Standards", by L.S. Zevin, J. Appl. Cryst., vol. 10, (1977) pp. 147–150.

International Tables for Crystallography, vol. C, 1992, Section 6.1, p. 476.

*Primary Examiner*—David P. Porta
*Attorney, Agent, or Firm*—Tony E. Piotrowski

[57] ABSTRACT

A method of determining the concentrations of the constituents in a mixture of substances by way of an X-ray diffractogram of the mixture. The fundamental difficulty that it is not possible to determine the entire power spectrum (PS) of the diffraction is avoided by making a suitable estimate of the PS on the basis of the diffractions that can be observed. Using an estimate of the dispersive power of the individual atoms in the unity cells of the constituents and the PS, the absolute intensities are determined from the relative intensities and on the basis thereof the concentrations of the constituents in the mixture are determined.

7 Claims, 2 Drawing Sheets

METHOD OF STANDARD-LESS PHASE ANALYSIS BY MEANS OF A DIFFRACTOGRAM

The invention relates to a method of determining the concentrations of the constituents in a mixture of substances, in which for each of the substances the set of associated diffraction reflections is identified in a radiation diffractogram of the mixture and the relative intensities of each set of diffraction reflections are determined.

A method of this kind is described in an article in "Journal of Applied Crystallography" (1977), Vol. 10, pp. 147–150: "A Method of Quantitative Phase Analysis without Standards" by L. S. Zevin.

In order to determine the composition of a mixture of different phases, such a mixture can be subjected to diffraction, for example X-ray diffraction. In this context the term "phase" is to be understood to mean a component of the mixture which causes own, characteristic diffraction reflections (also referred to as diffraction lines or lines for short) in the diffractogram. Thus, a phase may be a component formed by a substance having a separate chemical composition, or a substance which does not deviate from another component of the mixture in respect of chemical composition but only in respect of crystalline appearance. Quantization of the various phases of a mixture, i.e. the determination of the quantity of matter of the components in the mixture on the basis of a diffractogram of the mixture, generally involves the problem that some information on the mixture should be available in advance so as to enable the quantization to be performed. Existing methods of quantization can be split into two groups, i.e. the methods which utilize a standard and the methods which can be performed without a standard.

In order to carry out a method involving a standard, it is necessary that in the case of a mixture of n phases the diffractogram (i.e. the positions of the reflections and also their absolute intensities) should be known for at least n−1 phases. This data can be determined experimentally as well as theoretically, for example by means of computer simulation. In many cases, however, such data is not available, for example because the structure of several components of the mixture is not known and these components are not separately available either, as is some times the case for natural minerals.

In order to carry out a method without standards, it is necessary to know in advance only the positions of the reflections of n−1 phases and not their intensities. Therefore, these methods are the only ones that can be used in case the individual components are not available in a pure form, or if it is impossible to prepare a sample with known fractions of the components. An example of such a method is formed by the method described in the cited article by Zevin. The cited article describes a method which enables determination of the concentrations of the constituents in a mixture of substances without using standards. This known method, however, has a number of drawbacks. A first drawback, as is also mentioned in the section "Discussion and Conclusions" of the cited article, is that the reliability of the analysis result is strongly degraded when the absorption contrast becomes low. The latter is practically always the case for mineralogical and organic materials (notably pharmaceutical materials). Further drawbacks are that with this known method generally the effective absorption coefficient is unknown, that the effect of texture in the specimen may be high, and that n measurements must be performed for a sample containing n components.

It is an object of the invention to provide a method of standard-less phase analysis by means of a diffractogram of the kind set forth which enables a reliable determination of the concentrations of the constituents to be performed also in the case of a mixture containing constituents with a low absorption contrast.

To this end, the method according to the invention is characterized in that for each substance the total relative dispersive power (the relative power spectrum) is determined from the relative intensities, for each substance the volume integral of the square of the electron density is determined from its chemical compositional formula, and for each substance a scale factor is determined which is equal to the ratio of said volume integral to the relative power spectrum, said scale factor being used to determine the concentration of each of the constituents of the mixture.

The invention is based on the recognition of the fact that in the case of diffraction the total dispersive power per quantity of material can be predicted on theoretical grounds. This insight will be described in detail hereinafter. The invention also offers the additional advantages that the effective absorption coefficient need not be known, that the texture in the sample practically has no effect on the result, and that a single measurement suffices also for a sample containing n components.

In a version of the invention the relative power spectrum is determined from the measured relative intensities by extrapolation. Thus, only one parameter of the extrapolation function need be determined in the process of adapting the theoretical variation to the known variation.

In a further version of the invention the extrapolation function of said extrapolation contains the Fourier transform of the electron density of the individual atoms of the relevant constituent. This function can be readily determined from known volumes of tables in which these electron densities are stated in the form of tables. Computer algorithms which are known per se are available so as to derive the Fourier transform thereof.

In another version of the invention, said extrapolation function contains a term which is dependent on the temperature of the relevant substance. When it is known which theoretical variation of the total dispersive power is to be expected, the adaptation of the function representing this total dispersive power becomes more accurate and easier. Such higher accuracy is achieved by addition of said temperature-dependent term.

In a further version of the invention, for each substance the volume integral of the square of the electron density is determined from its chemical structural formula. As a result of the use of the structural formula instead of merely the general compositional formula, more information is obtained as regards the crystallographic structure of the substance to be analyzed. Thus, a higher accuracy can be achieved in determining the volume integral of the square of the electron density, so a higher accuracy in determining the concentrations of the constituents of the mixture to be analyzed. In another version of the invention a known concentration of a known substance is added to the sample. This method is suitable for those cases in which the mixture to be analyzed contains amorphous constituents. The concentrations of the crystalline constituents of the mixture can then be determined by adding a known concentration of a known substance to the sample; the scale factor and the relative intensities of the diffraction lines of said known substance must then be known. This is again a case of standard-less analysis, because it does not require a standard of the phases to be analyzed in the mixture.

As has already been stated, the insight on which the invention is based will be described in detail hereinafter. In the case of X-ray diffraction performed on a crystalline substance it is in principle impossible to determine the total reflected intensity. This impossibility also holds when all intensities associated with all diffraction angles ν from ν=0 to ν=2π, which are known from the Bragg relation 2.d.sinν= n.λ (d=distance between the lattices of the crystal) are traversed while forming the diffractogram. This phenomenon can be readily understood by considering the known lattice factor $\vec{G}$ which, as is known, defines all possible reflections in a given crystal lattice. Because it holds for the absolute value $|\vec{G}|$ that $|\vec{G}|=1/d$ and that according to the Bragg relation it must hold that $1/d \leq 2/\lambda$, it appears that only those reflections can be observed for which it holds that $|\vec{G}| \leq 1/d$. Thus, there is a fundamental upper limit in respect of observations associated with $|\vec{G}|$. The physical consequence thereof is that the values of $|\vec{G}|$ for which it holds that $|\vec{G}|>1/d$ do not lead to an observable diffraction reflection (or line).

The above fundamental difficulty can be circumvented on the basis of the insight underlying the invention by making an estimate of the overall dispersive power on the basis of the diffraction reflections (lines) that can be observed. The following approach is then used. The starting point is the assumption that the overall appearance of the curve representing the mean variation of the intensity of the diffraction lines associated with all values of $|\vec{G}|$ as a function of $|\vec{G}|$ is known on theoretical grounds, be it that the appearance and the situation of the relevant phase must still be determined by parameters which are dependent on the sample. The latter parameters can be determined, by extrapolation, from the observed diffraction lines and the chemical composition of the sample which is assumed to be known.

The foregoing is elaborated as follows. For the observed absolute intensity $I_i$ of a diffraction line of a phase it holds that:

$$I_i = K.A.S.I_{i,rel}.c \quad (1)$$

Therein, K is a constant which is dependent only on the diffractometer used, A is the absorption coefficient of the relevant substance; S is a scale factor which establishes the relationship between the observed relative intensity $I_{i,rel}$ of a line (i.e. the intensity of a line expressed in the intensity of another line, preferably that having the highest intensity) and the absolute intensity $I_i$ thereof, and c is the concentration of the relevant phase in the mixture to be examined.

Generally speaking, the values of $I_{i,rel}$ of a phase are known from tables (or can be measured). By way of example it is assumed that the mixture of phases to be analyzed consists of only two phases D and E, and that the mixture does not contain amorphous constituents. The variables in the expression (1) can thus be provided with an index D or E when they relate to the phases D and E, respectively. It then follows from the expression (1) that:

$$\frac{I_{i,D}}{I_{i,E}} = \frac{S_D \cdot I_{i,rel,D} \cdot c_D}{S_E \cdot I_{i,rel,E} \cdot c_E} \quad (2)$$

The latter expression shows that the factor K.A has been eliminated because this factor is the same for both phases in the mixture. (The absorption coefficient is dependent only on the nature of the relevant mixture.) It may also be that the variables A and K are different, for example because measurement has been performed by means of two different apparatus and/or because measurements have been performed on different samples; in that case the ratio of the factors K.A must be known, for example by mutual calibration. For the assumed two-phase mixture it also holds that $C_D+C_E=1$ (because there is no amorphous constituent). The left term of this equation (2) can then be determined by measurement. The ratio of the relative intensities is known so that, if the ratio of the scale factors $S_D$ and $S_E$ were known, the ratio of the concentrations could be determined and the individual values of $C_D$ and $C_E$ could be determined by means of the equation $C_D+C_E=1$. It is to be noted that the above two-phase situation, given by way of example, can be generalized to a situation involving an arbitrary number of n phases. In that case there are n−1 expressions which are analogous to the expression (2) plus an expression which indicates that the sum of the concentrations of each of the phases equals 1. The problem has thus been reduced to the determination of the scale factor S for each of the phases.

The following procedure can be used to determine the scale factor S of a phase. The total intensity that can be taken into account for diffraction is found using the square of the Fourier transform of the charge distribution of the electron clouds of the substance subject to diffraction present in the relevant volume V. The square of the Fourier transform can be written as follows:

$$I(\vec{G}_i) = \left| \int_V \vec{dr} \cdot \rho(\vec{r}) \cdot \exp(2\pi i \vec{G} \cdot \vec{r}) \right|^2 \quad (3)$$

in which $\vec{r}$ is the position vector within the volume V, $\rho(\vec{r})$ is the charge distribution in the relevant volume, and $\vec{G}$ is the reciprocal lattice vector. When the charge distribution $\rho(\vec{r})$ is periodic (as in the case of a crystalline substance), $I(\vec{G})$ consists of a series of discrete values which constitute the diffraction reflections upon diffraction. This means that the total dispersive power $I_{tot}$ can be written as:

$$I_{tot} = \sum_{i=1}^{i=\infty} I(\vec{G}_i) \quad (4)$$

In the expression (2), therefore, summing has been performed over all possible vectors $\vec{G}_i$ from the volume subjected to diffraction, so that the total dispersive power is obtained. This approximately infinite (because summing takes place over a very large number of the order of magnitude of $10^{23}$ vectors $\vec{G}_i$; the number $10^{23}$ stems from the Avogadro number) series of intensities, which are dependent on $\vec{G}_i$ (so $I(\vec{G}_i)$), of diffraction reflections is called the power spectrum. Because of the above restriction $|\vec{G}| \leq 1/d$, in a practical situation it is not possible to observe the entire power spectrum, but only a part thereof; in that case:

$$I(\vec{G})_{part} = \sum_{i=1}^{i=N} I(\vec{G}_i) \quad (5)$$

which shows that only N reflections are observed in this partial spectrum. This partial series of diffraction reflections is called the intensity spectrum. On the other hand, use can be made of a mathematical theorem which is known as the so-called power theorem:

$$\int_V \vec{dr} \cdot \rho^2(\vec{r}) = \sum_{i=1}^{i=\infty} \tilde{I}_i \quad (6)$$

in which $\tilde{I}_i$ is the intensity of the $i^{th}$ reflection which has been corrected for polarization. It appears from the expression (2) that only the product $S.I_{i,rel}$ in this expression is of importance to determine the absolute intensity $I_i$; on the basis thereof, the expression (6) can be written as:

$$\int_V \vec{dr} \cdot \rho^2(\vec{r}) = S \cdot \sum_{i=1}^{i=\infty} \tilde{I}_{i,rel} \cdot \varphi \quad (7)$$

in which $\varphi$ is a correction factor for the polarization which can be determined in known manner.

If the power spectrum which is still unknown could be determined and also the left term of the expression (7) which is also unknown as yet, the scale factor S would be known so that the problem posed would have been solved in principle.

On the basis of the known intensity spectrum the still unknown power spectrum can be obtained by making an extrapolation of the intensity spectrum according to the invention in such a manner that a suitable approximation of the power spectrum is obtained. In order to perform this approximation, the known assumption is made that $I_i(\vec{G})$ decreases with $|\vec{G}|$ in the way of the Fourier coefficients of the charge density of the electron clouds of the individual atoms in the crystallographic unity cell. A suitable estimate of the variation of the curve $I(\vec{G})$ as a function of $|\vec{G}|$ can be derived therefrom. A further, physical cause of the decrease of said curve is due to a temperature effect where the two factors combine as a product; this can be expressed in the form of a formula as:

$$I(|\vec{G}|) = \exp(-BT|\vec{G}|^2) \cdot FT[\rho(\vec{r})] \quad (8)$$

in which the coefficient B in the exponential part of the expression (8) constitutes the parameter whose variation realizes the fitting of the curve to the relevant measured points (so the values of $I_{i,rel}$)

A suitable determination of the as yet unknown left term of the expression (7) can be achieved according to the invention by using a method which is known per se.

This method implies that the integral in the left-hand term is determined from the known charge density distributions of the constituent electron clouds in the crystallographic unity cell. For a chemical compound a weighted contribution of the individual atoms in the compound is used, the weight factor being derived from the chemical compositional formule (so, for example, in $CaCl_2$, Cl is weighted twice as much as Ca).

Because the left term of the expression (7) is now known, like the power spectrum of the right term of the expression (7), the scale factor S can be determined for each of the phases in the mixture. The concentrations $C_D$ and $C_E$ in the expression (2) can thus be solved.

It has been assumed in the foregoing that the mixture to be analyzed does not contain amorphous constituents. However, if it does, the equation $C_D + C_E = 1$ is no longer valid. However, in that case it is still possible to perform a determination of the concentrations of the crystalline constituents of the mixture by adding a known concentration of a known substance to the sample, for example 0.1% $Al_2O_3$. The scale factor S and the various $I_{i,rel}$ values of this substance must then be known. Using the value of S which is now known, the factor K.A can be determined from the expression (1). Using the expression (7), the scale factor S can be determined for the unknown phase, after which the concentration of the unknown phase can be determined by means of the expression (1).

The invention will be described in detail hereinafter with reference to the Figures. Therein:

Figure 1:
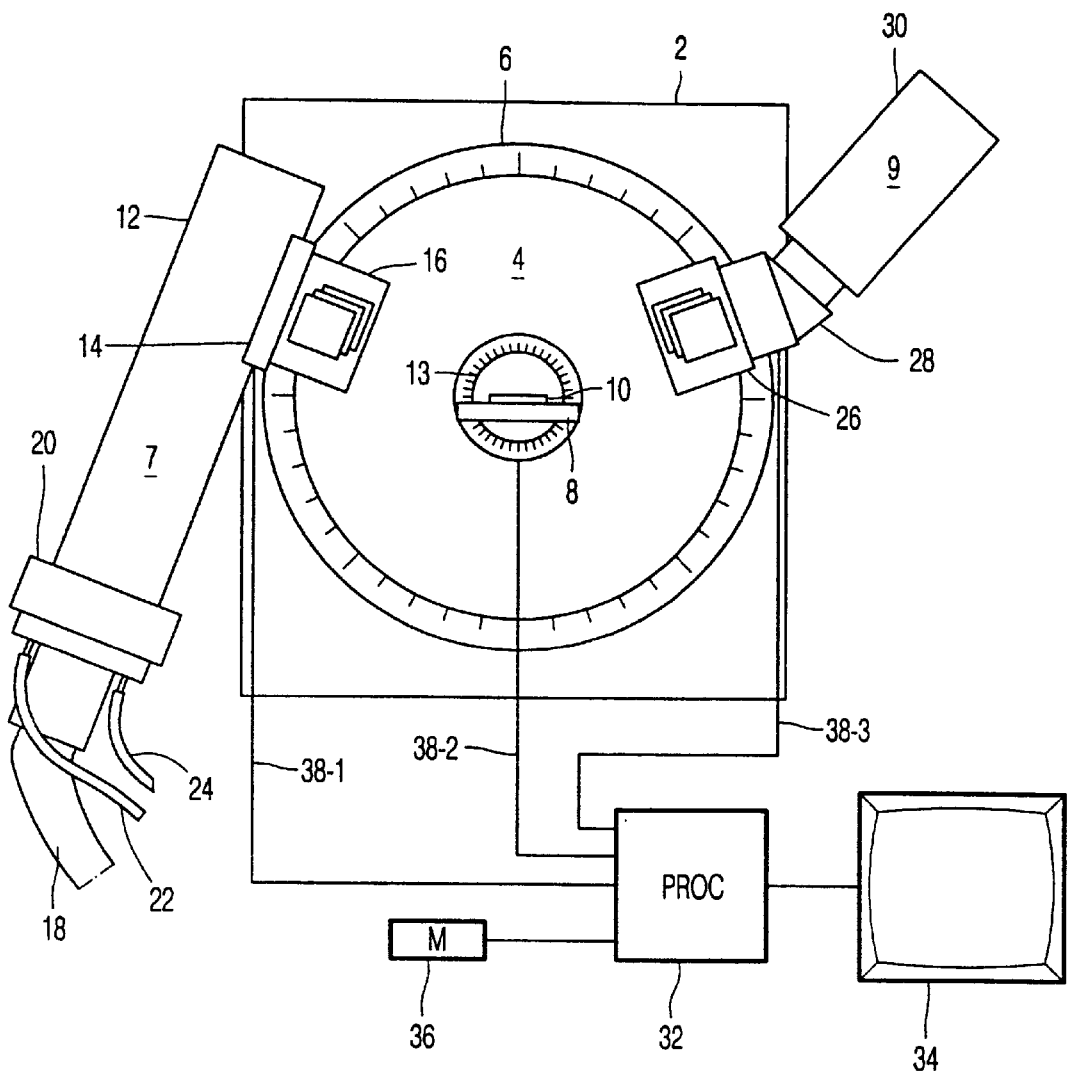
FIG. 1 shows diagrammatically an X-ray diffraction device according to the invention.

FIG. 1 shows an X-ray diffraction device in which agoniometer 4 is mounted on a frame 2. The agoniometer 4 is provided with a scale graduation 6 for measuring the angular rotation of the X-ray source 7, being mounted thereon, and of the detector device 9 which is also mounted thereon. The agoniometer, moreover, is provided with a sample holder 8 on which a sample 10 is arranged. For cases where measurement of the angular rotation of the sample is important, a scale graduation 12 is provided. The X-ray source 7 includes a holder 12 for an X-ray tube (not shown in the Figure) which is secured in the holder by way of a fixing ring 20. The X-ray tube includes a high-voltage connector 16 via which the high voltage and the filament current for the X-ray tube are supplied via the high voltage cable 18. Supply and discharge ducts 22 and 24 for the cooling water of the X-ray tube are provided at the same side of the X-ray tube. The tube holder 12 also comprises an exit window for X-rays 14 and a unit 16 for parallelization of the X-ray beam (a Soller slit). The detector device 9 consists of a holder 26 for a Soller slit, a holder 28 for a monochromator crystal, and a detector 30. If the X-ray source as well as the detector is rotatable about the sample, as shown in the Figure, it is not necessary for the sample to be arranged so as to be rotatable. However, it is alternatively possible to mount the X-ray source so as to be stationary, as may sometimes be necessary in the case of voluminous and heavy X-ray sources. In that case the specimen holder as well as the detector should be rotatable.

The X-ray diffraction device as shown in FIG. 1 also includes a processing device for processing the various measured data. The processing device consists of a central processing unit 32 whereto a memory unit 36 and a monitor 34 for the presentation of the various data and for the display of the measured and calculated result are connected. It will be evident that the memory unit 36 need not be separately constructed and that it may form part of the central processing unit 32. The X-ray source 7, the detector device 9 and the specimen holder 8, mounted on the agoniometer 4, are all provided with a unit (not shown) for determining the angular position of the relevant element with respect to the scale graduation of the agoniometer. A signal representing this angular position is applied, via connection leads 38-1, 38-2 and 38-3, to the central processing unit 32. The memory unit 36 stores the data required to carry out the analysis as will be described in detail with reference to FIG. 2. Using the X-ray diffraction device shown in FIG. 1, a diffractogram of the mixture to be quantified is formed in known manner, i.e. the intensity and the angular position of the various diffraction lines are determined by traversing the entire angular range $0 \leq v < 2\pi$.

Figure 2:
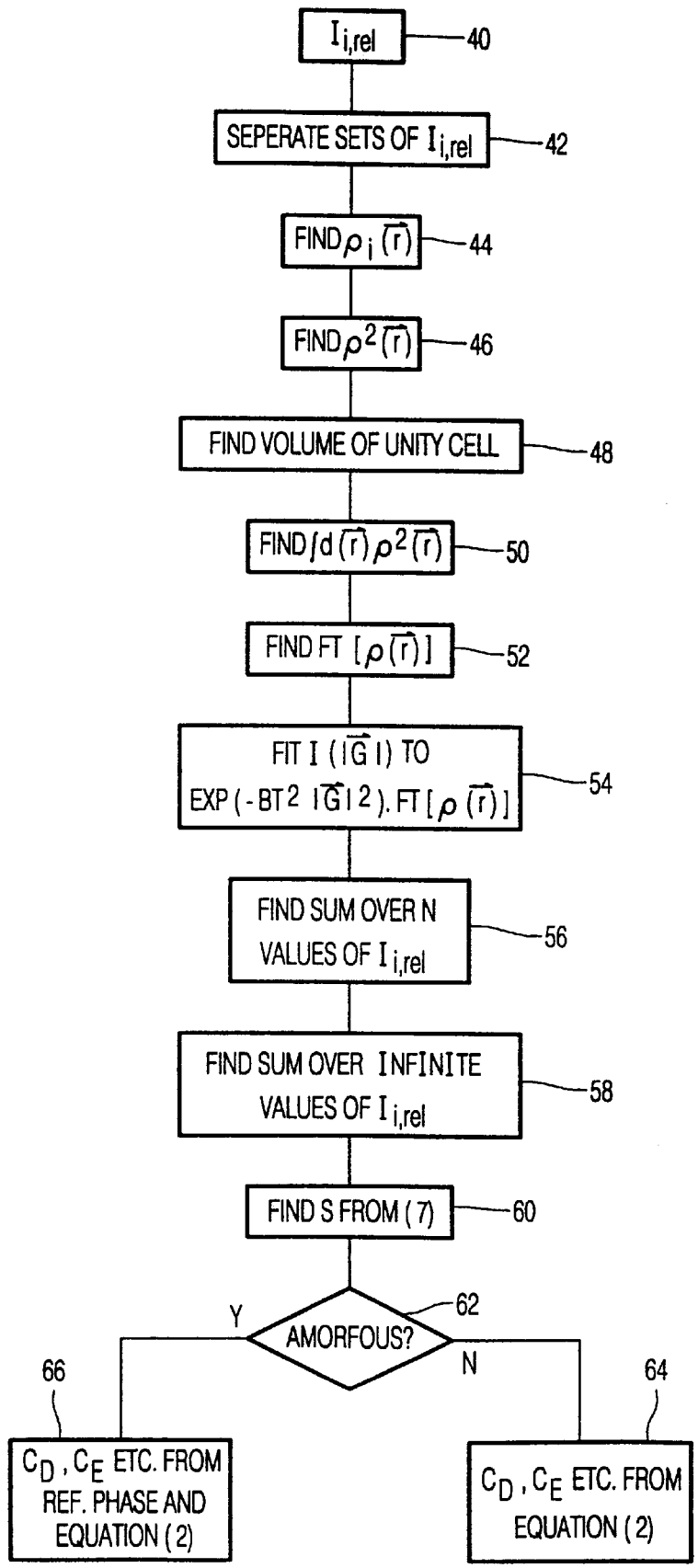
FIG. 2 shows a flow chart illustrating the various steps of the method according to the invention.

FIG. 2 shows a flow chart illustrating the various steps carried out to determine the concentrations of the constituents of the mixture to be quantified from the X-ray diffractogram formed. It is assumed that a diffractogram of a mixture to be quantified, consisting of a number of phases, is available. The diffractogram consists of a number of diffraction reflections or diffraction lines, each of which has its own intensity. The relative intensity $I_{i,rel}$ of each of these diffraction lines is determined (40), i.e. the intensity of a diffraction line expressed in the intensity of the diffraction lines of the total diffractogram which have the highest intensity.

The total diffractogram consists of a number of completely or partly overlapping sets of diffraction lines, each time one set being associated with a phase of the mixture to be quantified. Because, generally speaking, the diffractogram of each of the phases (i.e. the values of $I_{i,rel}$ and the location of the diffraction lines) is known (for example, from tables or by measurement performed on a pure phase), the total diffractogram can be split into the separate sets of diffractograms, each of which is associated with one of the phases (42).

In the subsequent blocks (44)–(50) of the flow chart an estimate of the variable $\int d(\vec{r})\rho^2(\vec{r})$, (see the expressions (6) and (7), is made per atom in the unity cell, the integration extending across the volume of the unity cell. To this end, for each atom i in the chemical compositional formula first the value of the charge density $\rho_i(\vec{r})$ of the electron cloud is determined. This determination can be performed in two ways. A first method utilizes an algorithm which is known as "Hartree-Fock calculations". This method is known from "International Tables for Crystallography", Vol. C, Kluwer Academic Publishers, 1992, paragraph 6.1.1.3. According to this known method, the atomic number $Z_i$ is used as input and the charge density $\rho_i(\vec{r})$ is obtained as a function of the position vector $\vec{r}$. Because the result is spherical symmetrical, it may be simply stated that $\rho_i$ is obtained as a function of r. According to this Hartree-Fock method the volume of each of the atoms i, as required subsequently, is also obtained. According to the alternative method of determining the charge density as a function of r, use is made of generally known tables in which these values are stated in tabular form. The array of values (i.e. $\rho$ as a function of r) obtained by means of one of the described methods can then be stored in the memory 36 wherefrom they can be fetched as required for processing by the computer program. The block 44 in the flow chart represents the acquisition of the charge density $\rho_i(\vec{r})$ as a function of the position vector $\vec{r}$.

When $\rho_i$ as a function of r is known for each of the atoms in the chemical compositional formula, a suitable approximation of the variable $\rho^2(\vec{r})$ can be obtained for the total number of atoms in the chemical compositional formula by summing the values $\rho_i^2(\vec{r})$ for each of the atoms, see block 46. In order to obtain the volume over which the integration should extend, the N volumes $V_{i,at}$ of the N individual atoms, already obtained by means of the Hartree-Fock method are summed, so that a suitable approximation of the volume $V_e$ of the unity cell is obtained, see block 48. The array of values already obtained, i.e. $\rho$ as a function of r stored in the memory 36, is then used for the numerical execution of the integration. The integration implies that the variable $\rho^2(\vec{r})$ is continuously multiplied by the infinitely small volume of a shell of a sphere $4\pi r^2 dr$ and the products thus obtained are accumulated. The integration is then executed over the volume of the unity cell, i.e. integration continues until such a value of r is reached that the volume determined for the unity cell is reached, so until r has a value such that $V_e=(4/3)\pi r^3$. This procedure is symbolically represented in the block 50. When this integral value is known, the left term of the expression (7) is known and available.

During the subsequent blocks (52)–(60) of the flow chart the scale value S is determined for each phase of the mixture to be quantified. To this end, first the Fourier transform $FT[\rho(\vec{r})]$ is determined. The variables $\rho(\vec{r})$ were already known: see the blocks 44 and 46 in which these variables have been obtained as an intermediate result yielded by the summing over the atoms of the chemical compositional formula. The execution of the Fourier transformation of these variables (block 52) is a generally known method which need not be elaborated herein. This transformation yields an array of values of $FT[\rho(\vec{r})]$ as a function of $|\vec{G}|$.

The left term of the expression (8) is known, because $I(|\vec{G}|)$ is the array of relative intensities per phase as already determined, see block 42. The function values in this array are a function of $|\vec{G}|$, or of 2v, being the diffraction angle. In the right term of the expression (8) the factor $\exp(-BT.|\vec{G}|^2)$ is not known, but in this factor the value of B is determined by adapting this unknown function to the other known variables in this expression, see block 54.

The procedure used to find the scale value S is as follows. First the series of known intensities $I_{i,rel}$ is assumed to be a curve as a function $|\vec{G}|=G$, the initial value of G being set to $G_0$ and the final value (so of the last diffraction line measured) to $G_1$. After that it is assumed that the surface area below said curve, between $G_0$ and $G_1$, is equal to a constant K times the sum of the measured values $I_{i,rel}$; block 56. Subsequently, the sum of the intensities of $G_0$ to $G=\infty$ can be determined by assuming that K times the latter sum equals the surface area below said curve from $G_0$ to $G=\infty$; this surface area is known because the value of B is known due to adaptation of the curve, so the entire course of the curve; block 58. The sum of the intensities from $G_0$ to $G=\infty$ can then be inserted in the right term of the expression (7). (The introduction of the correction factor $\phi$, for example known from tables, for the polarization is generally known and need not be elaborated.) Because the left term of the expression (7) was already known (see block 50), the scale value S can now be determined, that is to say for each phase of the mixture to be quantified, block 60.

When the mixture to be quantified does not contain amorphous phases (block 62), the concentrations $C_D$, $C_E$ etc. of the phases can be determined by means of these known scale values $S_D$, $S_E$ etc., see block 64. When the mixture to be quantified does contain an amorphous phase (block 62), a known concentration of a known reference substance must be added to the sample, for example 0.1% $Al_2O_3$. The scale factor S and the various values of $I_{i,rel}$ of this substance must be known. Using the known value of S, the factor K.A in the expression (1) can be determined and, using the expression (7), the scale factor S can be determined for the unknown phases, after which the concentration of the unknown phase can be determined by means of the expression (1), see block 66.

The effect of the method according to the invention has been tested by means of computer simulation. The simulation was based on a sample of a mixture of two known phases, $SiO_2$ and $PbO_2$, a known concentration $c_{act}$ of 50% of each of which was present in the sample. The estimated scale factors $S_{est}$ have been determined by means of the method; the actual scale factors $S_{act}$ have been calculated, and subsequently the concentrations $c_{est}$ estimated according to the method have been determined. The results are shown in the following Table:

| phase | $S_{est}$ | $S_{act}$ | $C_{est}$ | $C_{act}$ |
|---|---|---|---|---|
| $SiO_2$ | 4.75 | 4.2 | .48 | .50 |
| $PbO_2$ | 19.62 | 18.1 | .52 | .50 |

The good correspondence of the values of $c_{act}$ and $c_{est}$ demonstrates that the method according to the invention offers a reliable estimate of the concentrations in the mixture.

What is claimed is:

1. A method of determining the concentrations of the constituents in a mixture of substances, in which:

for each of the substances (42), the set of associated diffraction reflections is identified in a radiation diffractogram of the mixture, and the relative intensities of each set of diffraction reflections are determined (40), characterized in that for each substance the total relative dispersive power (the relative power spectrum) is determined from the relative intensities (58), for each substance the volume integral of the square of the electron density is determined from its chemical compositional formula (50), and for each substance a scale factor S is determined, which is equal to the ratio of said volume integral to the relative power spectrum, said scale factor being used to determine the concentration of each of the constituents of the mixture (60).

2. A method as claimed in claim 1, in which the relative power spectrum is determined from the measured relative intensities by extrapolation (58).

3. A method as claimed in claim 2, in which the extrapolation function of said extrapolation contains the Fourier transform of the electron density of the individual atoms of the relevant constituent (52).

4. A method as claimed in claim 3, in which said extrapolation function contains a term which is dependent on the temperature of the relevant substance (54).

5. A method as claimed in claim 1, in which for each substance the volume integral of the square of the electron density is determined from its chemical structural formula (50).

6. A method as claimed in claim 1, in which a known concentration of a known substance is added to the sample (66).

7. An apparatus for diffraction analysis which includes:

a sample holder (8) for accommodating a sample (10) of a mixture of substances to be examined, a radiation source (7) for irradiating the sample location by means of analysis radiation, a detector (9) for detecting the diffracted radiation emanating from the sample, which apparatus includes means (7, 8, 9) for forming a radiation diffractogram of the sample (10), characterized in that the apparatus is provided with means (32, 36) for identifying the sets of diffraction reflections associated with each of the substances, the apparatus is provided with means (32, 36) for determining the relative intensities of each of the sets of diffraction reflections, the apparatus is provided with means (32, 36) for determining the relative power spectrum for each substance from the relative intensities, the apparatus is provided with means (32, 36) for determining the volume integral of the square of the electron density for each substance from the chemical compositional formula of the substance, the apparatus is provided with means (32, 36) for determining for each substance a scale factor which is equal to the ratio of said volume integral to the relative power spectrum, the apparatus is provided with means (32, 36) for determining the concentration of each of the constituents of the mixture from the scale factor thus determined.

* * * * *